United States Patent
Obradovic et al.

(10) Patent No.: US 7,984,636 B2
(45) Date of Patent: Jul. 26, 2011

(54) APPARATUS AND METHODS FOR MEDICAL DEVICE EXPANSION

(75) Inventors: Milisav Obradovic, Lörrach (DE); Rainer Bregulla, Balingen (DE)

(73) Assignee: Abbott Laboratories, Abbott Park, IL (US)

( * ) Notice: Subject to any disclaimer, the term of this patent is extended or adjusted under 35 U.S.C. 154(b) by 171 days.

(21) Appl. No.: 11/959,372

(22) Filed: Dec. 18, 2007

(65) Prior Publication Data

US 2009/0151416 A1 Jun. 18, 2009

(51) Int. Cl.
*B21D 39/08* (2006.01)
*B21D 41/02* (2006.01)

(52) U.S. Cl. .................... 72/370.07; 72/393; 72/466

(58) Field of Classification Search .. 72/370.06–370.08, 72/392, 393, 31.06, 367.1, 342.1, 466, 466.2, 72/466.8; 623/1.12, 1.2
See application file for complete search history.

(56) References Cited

U.S. PATENT DOCUMENTS

| | | | | | |
|---|---|---|---|---|---|
| 8,256 | A | * | 7/1851 | McCarty | 72/393 |
| 2,621,053 | A | * | 12/1952 | Kane | 279/2.03 |
| 3,774,429 | A | * | 11/1973 | Holzer | 72/370.06 |
| 4,212,187 | A | * | 7/1980 | Scholz | 72/393 |
| 4,387,845 | A | * | 6/1983 | Mefferd | 228/222 |
| 5,907,893 | A | * | 6/1999 | Zadno-Azizi et al. | 29/6.1 |
| 6,412,766 | B2 | * | 7/2002 | Barbieux | 269/48.1 |
| 7,112,055 | B1 | * | 9/2006 | Anukhin et al. | 425/365 |
| 2007/0288034 | A1 | * | 12/2007 | MacCollum et al. | 606/108 |
| 2008/0066518 | A1 | * | 3/2008 | Glenn et al. | 72/370.07 |

* cited by examiner

*Primary Examiner* — Edward Tolan
*Assistant Examiner* — Pradeep C Battula
(74) *Attorney, Agent, or Firm* — Workman Nydegger

(57) ABSTRACT

A mandrel usable for expanding a medical device is disclosed. The mandrel includes a first tube portion having a first lumen and a first tube diameter. A second tube portion extends from the first tube portion; the second tube portion is configured to receive a medical device. A second tube diameter is smaller than the first tube diameter. A plurality of tube segments are separated by a plurality of slots formed in the mandrel, while a second lumen is in communication with the first lumen. At least a portion of the plurality of tube segments is moveable outwardly to expand the medical device.

21 Claims, 4 Drawing Sheets

APPARATUS AND METHODS FOR MEDICAL DEVICE EXPANSION

BACKGROUND OF THE INVENTION

I. The Field of the Invention

The present invention generally relates to the field of medical devices. More specifically, the present invention relates to methods, systems, and devices for manufacturing a self-expanding medical device.

II. Related Technology

The use of intravascular devices to treat cardiovascular diseases is well known in the field of medicine. The need for a greater variety of devices to address different types of circumstances has grown tremendously as the techniques for using intravascular devices has progressed. One type of intravascular device is a stent. Stents are generally cylindrically shaped intravascular devices, which are placed within an artery (or other vessel within the body) to hold it open. The device can be used to reduce the likelihood of restenosis or recurrence of the blocking of a blood vessel. In some circumstances, a stent can be used as the primary treatment device where it is expanded to dilate a stenosis and left in place.

A variety of stent designs have been developed. Examples include coiled wires in a variety of patterns that are expanded after being placed within a vessel on a balloon catheter, helically wound coiled springs manufactured from expandable heat sensitive metals, stents shaped in zig-zag patterns, and self-expanding stents inserted in a compressed state for deployment in a body lumen. One of the difficulties encountered using stents involve maintaining the radial rigidity needed to hold open a body lumen while at the same time maintaining the longitudinal flexibility of the stent to facilitate its delivery and accommodate the often tortuous path of the patient's vasculature. Generally, the greater the longitudinal flexibility of the stent, the easier and more safely it can be delivered to the implantation site.

A stent can have various features. For instance, a stent can have a tubular shape formed from a plurality of interconnected struts and/or legs that can form a series of interconnected rings. In the expanded condition, the stent can have a cylindrical shape to expand in an artery. One preferred material for manufacturing self-expanding stents is NITINOL, an alloy of Nickel and Titanium.

NITINOL, an alloy of Nickel and Titanium, self-expanding stents can be manufactured in a variety of different manners. One typical approach is to laser cut the design of the stent from a tube which dimensions are close to the desired compressed size. The tube is then deburred to clean any imperfections due to the cutting. Cycles of stent expansion and heat treatment are then repeated until the stent reaches its intended dimension for deployment in a vessel.

Unfortunately, current manufacturing processes are cumbersome and in some instance induce cracks in the stent from undesired torque and compression. It is therefore, desirable, to provide a new method of manufacturing self-expanding stents.

BRIEF SUMMARY OF THE INVENTION

In one configuration, a mandrel usable for expanding a medical device is disclosed. The mandrel can included a first tube portion having a first lumen and a first tube diameter. Extending from the first tube portion is a second tube portion configured to receive a medical device. A diameter of the second tube portion is smaller than the diameter of first tube portion. The second tube portion includes a plurality of tube segments separated by a plurality of slots, at least a portion of the plurality of tube segments are moveable outwardly to expand the medical device. In communication with the first lumen is a second lumen formed in the second tube portion.

In another configuration, a system for manufacturing a medical device is disclosed. The system can include a mandrel having first tube portion and a second tube portion. The first tube portion can include a first lumen and a first tube diameter. Extending from the first tube portion is a second tube portion configured to receive a medical device. A diameter of the second tube portion is smaller than the diameter of first tube portion. The second tube portion includes a plurality of tube segments separated by a plurality of slots, at least a portion of the plurality of tube segments are moveable outwardly to expand the medical device. In communication with the first lumen is a second lumen formed in the second tube portion. An expansion member can be slidably received within at least a portion of the first lumen and the second lumen. The expansion member is advanceable within the second lumen to move the plurality of tube segments radially outwardly to expand the medical device.

In still another configuration, a system for manufacturing a stent is disclosed. The system can include a first mandrel having first tube portion and a second tube portion. The first tube portion can have a first lumen and a first tube diameter, while the second tube portion can have a second tube diameter smaller than the first tube diameter, a plurality of tube segments separate by a plurality of slots, and a second lumen in communication with the first lumen. The second tube portion is configured to receive the stent upon its outer surface. A second mandrel configured similarly to the first mandrel can be slidably received within at least a portion of the first lumen and the second lumen of the first mandrel. The second mandrel is advanceable within the second lumen to move the plurality of tube segments radially outwardly to expand the stent.

In still another configuration, a method of expanding the diameter of a medical device is disclosed. The method can include the steps of (i) positioning a first mandrel having a first tube portion and a second tube portion for receiving a medical device, a first tube portion diameter being larger than a second tube portion diameter, (ii) placing the medical device over a portion of the second tube portion, and (iii) inserting an expansion member within at least a portion of the first tube portion and the second tube portion, the expansion member increasing the second tube portion diameter to increase the diameter of the medical device. Further, the method can include inserting the expansion member comprises inserting a second mandrel configured similarly to the first mandrel or annealing the medical device upon the medical device being expanded by the first mandrel.

In still another configuration, the method can include, removing the expansion member from within at least a portion of the first tube portion and the second tube portion following annealing of the medical device and expanding the medical device upon a third mandrel to increase the outer diameter of the medical device. Further, the method can include placing the annealed medical device on the third mandrel have a third tube portion and a fourth tube portion, at least one of the third tube portion and the fourth tube portion having a diameter equal to or larger than the diameter of the first tube portion and the second tube portion and inserting another expansion member within at least a portion of the third tube portion and the fourth tube portion, the another expansion member increasing the fourth tube portion diameter to increase the diameter of the medical device.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

Generally, the invention relates to methods, systems, and devices for expanding a medical device in a controlled manner. The methods provided through the systems and devices are repeatable and reduce the possibility of incorrectly expanding medical devices during the manufacturing process. Further, the methods provided herein reduce the possibility of undesired torquing, compression, and squeezing of the stent during manufacture.

Figure 1A:
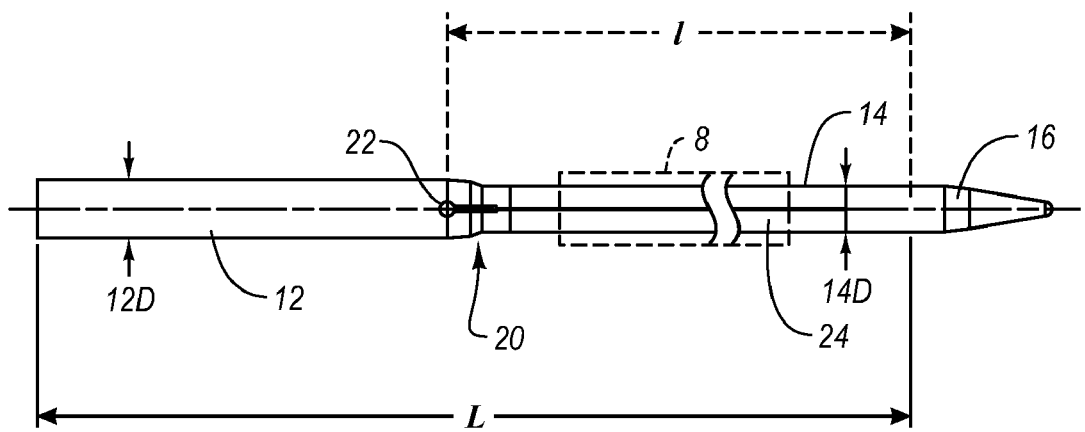
FIG. 1A shows a side view of a mandrel that is used to manufacture a self-expanding stent according to the present invention.
Figure 1B:
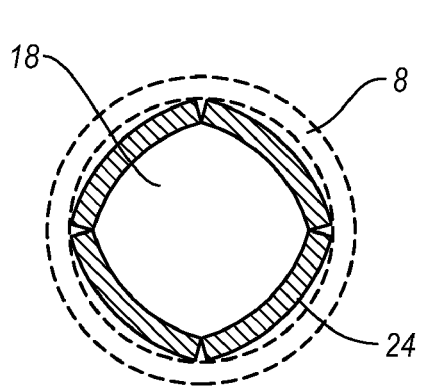
FIG. 1B is a cross-sectional side view of a portion of the mandrel of FIG. 1A.
Figure 1C:
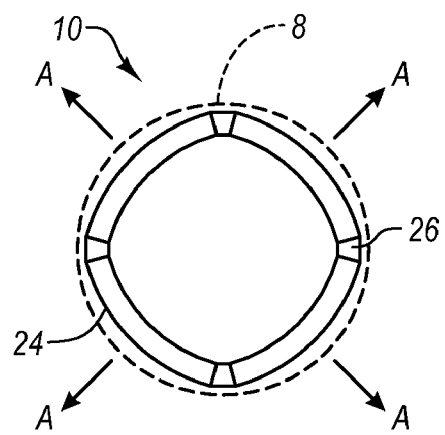
FIG. 1C is another cross-sectional side view of a portion of the mandrel of FIG. 1A.

Turning to FIGS. 1A-1C, illustrated is a mandrel 10 that is used to manufacture a self-expanding medical device, such as a self-expanding stent. The mandrel 10 includes a first tube portion 12, a second tube portion 14, a cone 16, and a lumen 18 extending from the first tube potion 12 toward the second tube portion 14. The first tube portion 12 has a diameter 12D, while the second tube portion 14 has a diameter 14D that is smaller than the diameter 12D. A transition region 20 transitions the diameter of the mandrel 10 from that of the first tube portion 12 to that of the second tube portion 14.

The second tube portion 14 of mandrel 10 includes a number of tube segments 24; the tube segments 24 being positioned to substantially match the inside diameter of the medical device 8, illustrated in phantom in FIGS. 1A and 1B. The tube segments 24 terminate adjacent the first tube portion 10 at the transition region 20 by way of opening 22, optionally circular in configuration. The tube segments 24 are separated one from another along substantially all their lengths from the transition region 20 toward the cone 16 to facilitate expansion of the medical device 8. For instance, movement of the separated tube segments 24 allows the diameter 14D of the second tube portion 14 to be increased upon insertion of a rod, pin, or another mandrel 10 within lumen 18 that moves the tube segments 24 radially outwardly, as will be discussed further hereinafter. The tube segments 24, therefore, can move in the direction of arrows A from the configuration illustrated in FIG. 1B to that illustrated in FIG. 1C, where a slot or gap 26 forms between adjacent tube segments 24. The size and configuration of the slot or gap 26 can be calculated based upon, for example, the diameter 12D of the first tube portion 12, the diameter 14D of the second tube portion 14, the amount of desired expansion of the tube segments 24, the length and chord length of each tube segment 24 and/or the desired gap. An example of such calculation is provided hereinafter.

Returning to FIG. 1A, mounted to the opposite ends of the tube segments 24 from transition region 20 is the cone 16 which limits movement of those ends during expansion of medical device 8. The cone 16 can be mounted upon the ends of the tube segments 24, receive a portion of the tube segments 24 within a lumen of the cone 16, or combinations thereof. Attachment of cone 16 can be achieved through welding, thermal bonding, adhesive bonding, interference fit, combinations thereof, or other techniques or methods to join to members together.

Generally, mandrel 10 can be fabricated from a variety of different materials. For instance, mandrel 10 can be made from metals, alloys, plastics, polymers, composites, combinations thereof, or other materials as desired based upon the particular medical device to form and the temperatures and/or pressures that the mandrel is to withstand during medical device manufacture. In one example, the mandrel can be fabricated from stainless steel or NITINOL, an alloy of Nickel and Titanium. In another example, the materials withstand a temperature from about 300° C. to about 550° C.

The mandrel 10 can have various lengths and configurations based upon the particular medical device being expanded through use of the mandrel. For instance, for a self-expanding stent, the tubular segments can have a length l=(length of stent+20 mm), while the length L of the mandrel is L=l+50 mm. It will be understood, however, the other lengths greater and lesser than those described are also possible. For instance, the length l of the tubular segments can be about 30 mm, while the length L of the mandrel can be about 80 mm. It will be understood that the lengths larger and/or smaller than 30 mm and 80 mm are possible depending upon the particular length of the medical device and/or the manufacturing processes associated with the fabrication of the medical device.

Figure 2A:
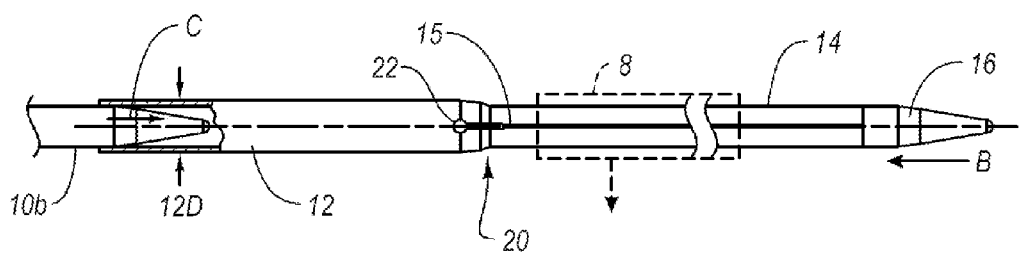
FIG. 2A shows a partial cross-sectional side view of the mandrel of FIG. 1A with a second mandrel partially inserted within the lumen of the mandrel.
Figure 2B:
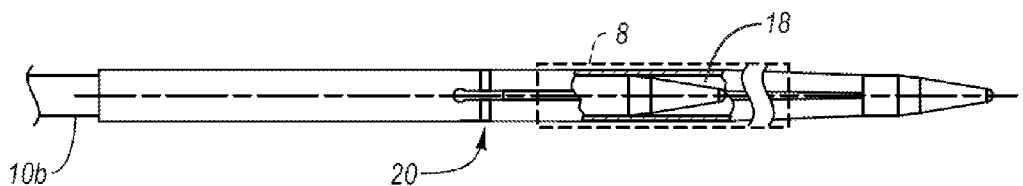
FIG. 2B shows a partial cross-sectional side view of the mandrel of FIG. 2A with the second mandrel more fully inserted within the lumen of the mandrel to expand the medical device.

Turning now to FIGS. 2A-2B, illustrated is the operation of the mandrel 10 in forming the medical device, such as a stent. As illustrated in FIG. 2A, a stent 8 is placed uniformly over the mandrel 10 from the side of the cone 16 and in the direction of arrow B. Following stent placement, a second mandrel 10b is introduced into lumen 18 of mandrel 10 in the direction of arrow C. As mandrel 10b is advanced toward the cone 16 and second tube portion 14 it begins to increase the diameter 14D of second tube portion 14. For instance, and as shown in FIG. 2B, as the mandrel 10b reaches the transition area 20 and the second tube portion 14, the mandrel 10b begins to cause movement of the tube segments 24 to increase the diameter 14D of the second tube portion 14. This movement increases the size of the slots or gaps 26 (FIG. 1C) in the second tube portion 14 and increases the outside diameter of the second tube portion 14. Consequently, the outside diameter of the stent 8 is increased. Shifting of the tube segments 24 in the radial direction, without torque, compression or squeezing, therefore drives the expansion of the stent 8.

The amount of expansion of the inside and outside diameter of the stent 8 can vary based upon the particular configuration of the mandrels and the materials used to form the stent. In one configuration, the first expansion step can be approximately 2 mm. That is, the distance between the diameter 12D of the first tube portion 12 and the diameter 14D of the second tube portion 14 is approximately 2 mm. It will be understood that other expansions greater and lesser than 2 mm are possible.

Upon reaching the desired stent outside diameter the mandrel 10, mandrel 10b, and the stent 8 can be heated to anneal the stent in the desired configuration. This process can be repeated using the same mandrel 10 or a combination of differently sized mandrels to achieve the final expanded configuration, with associated outside diameter, of the stent. For instance, the annealed and heat-set stent can be removed from one mandrel and placed on another mandrel having a larger outside diameter than the first, such as mandrel 10b; the stent being subsequently increased in diameter as the second tube portion diameter of this other mandrel is increased following a similar procedures as described above.

Figure 2C:
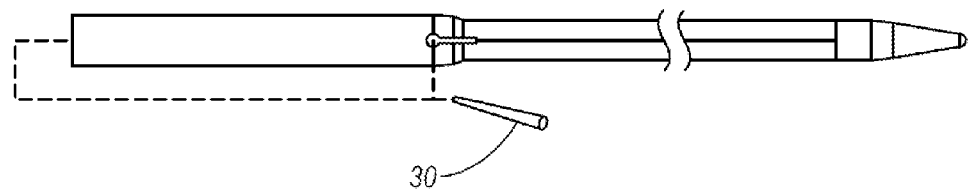
FIG. 2C shows a side view of the mandrel and associated expansion member usable to expand a second tube portion of the mandrel.

In an alternative configuration, a separate pin or expansion member 30 may be introduced into lumen 18 of the mandrel 10, as illustrated in FIG. 2C. The expansion member 30 can be elongated and function similarly to mandrel 10b above. For instance, advancing the expansion member 30 toward the cone 16 can increase the diameter of second tube portion 14.

Alternatively, the expansion member 30 can be inserted into the opening 22 and drawn or moved toward the cone 16 along the length of one or more of the slots or gaps 26 of the second tube portion 14. This increases the size of each slot or gap 26 and so increases the diameter of the stent.

The expansion member 30 can have various configurations to perform the identified function for moving the tube segments radially outwardly. In one configuration, the expansion member 30 has a generally circular cross-section. In other configurations, the expansion member 30 can have an oval, polygonal, or other cross-section that can be used to increase the outside diameter of at least the second tube portion of the mandrel.

Figure 3:
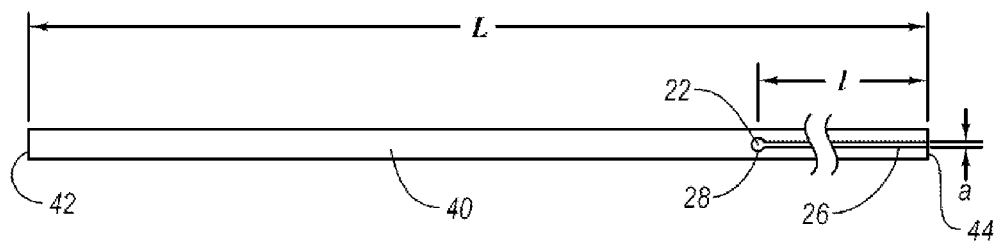
FIG. 3 shows an as cut side view of a mandrel usable to form the mandrel of FIG. 1A.

Turning now to FIG. 3, illustrated is one configuration of a mandrel pre-form or mandrel member usable to construct the mandrel 10. The structures and features of the mandrel member can be formed through use of one or more manufacturing techniques or methods, such as, but not limited to, milling, machining, laser cutting, water-jet cutting, electrical discharge machining (EMD), die casting, injection molding, or other techniques or methods for forming a structure fabricated from the previously identified materials.

As illustrated, the mandrel member 40 has a generally elongated configuration having a first end 42 and a second end 44. Extending from the second end 44 toward the first end 42 are the slots or gaps 26. Each slot or gap 26 has a width represented by the letter "a," which represents a cut-out portion of the circumference of the second tube portion 14. This slot or gap 26 can be sized based upon the particular inside diameter of the materials used to form the stent and the diameter of the mandrel member 40 used to expand the stent, as will be described in more detail hereinafter.

As described above, an end 28 of each slot or gap 26 has an opening or shape 22 having a diameter AD, this diameter being approximately 0.7 mm to about 1.0 mm. The opening 22 represents the beginning of each slot or gap 26 and reduces the strain of the slot or gap 26 upon the remainder of the mandrel member 40 during manufacture of the mandrel and/or use of the mandrel to increase the diameter of the stent. In this illustrated configuration of FIGS. 1A-1C, length l of the slot or gap 26 is defined by l=(length of stent+20 mm), while the length L of the mandrel is L=l+50 mm.

Following manufacture to the form illustrated in FIG. 3, the mandrel member 40 is mechanically treated to create the second tube portion 14 having the smaller diameter 14D than the diameter 12D of the first tube portion 12 and the slots or gaps 26 are formed, such as through laser cutting. After the mechanical treatment, etching of the first tube portion 12 and/or the second tube portion 14 occurs. For instance, the first tube portion can be etched in hydrofluoric acid (2%) and nitric acid (30-40%) for about 30-60 min at a temperature of about 40-70° C., optionally with ultrasonic assistance. Then, the cone 16 is attached to the second tube portion 14, as described above, to form the mandrel 10. The cone 16 aids compressing the tube segments 24 together and so reducing the size of the slot or gap 26 to substantially or generally zero.

It will be understood that there are various other methods and techniques for forming the mandrel and/or the mandrel member. These techniques can include extruding, molding, milling, etching, water-jet cutting, electrical discharge machining (EDM), die casting, injection molding, or the like.

Turn now to the width or size "a" of each slot or gap 26, the particular configuration of those slots or gaps 26 can be calculated in a variety of different manners. Following is one example of a method for calculating the desired width or size "a".

Figure 4A:
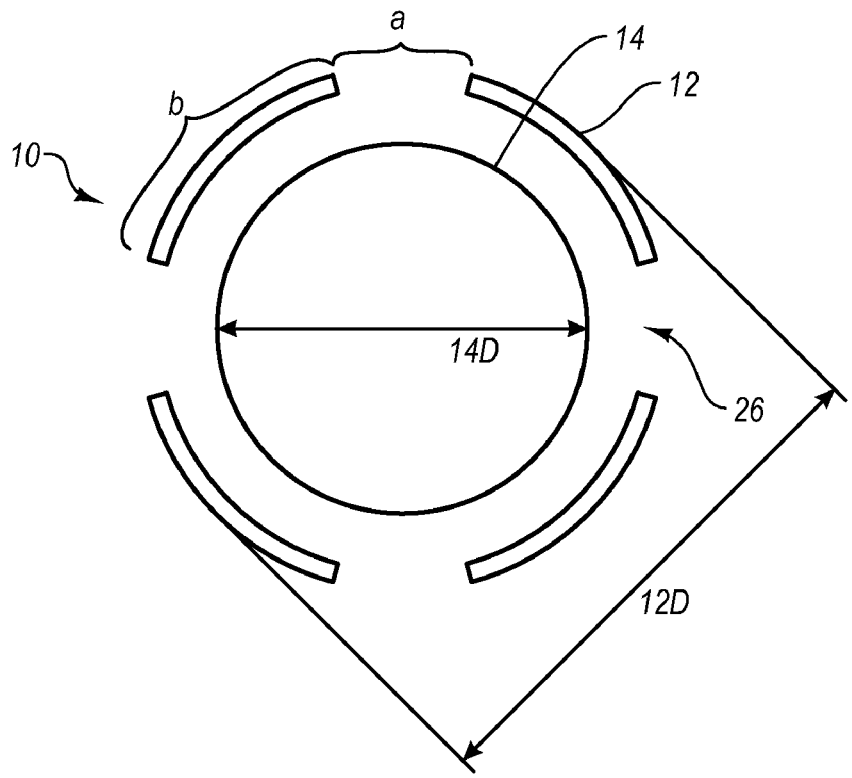
FIGS. 4A-4D schematically represents the expansion of the mandrel for use in calculating the gap or slot width or size.
Figure 4B:
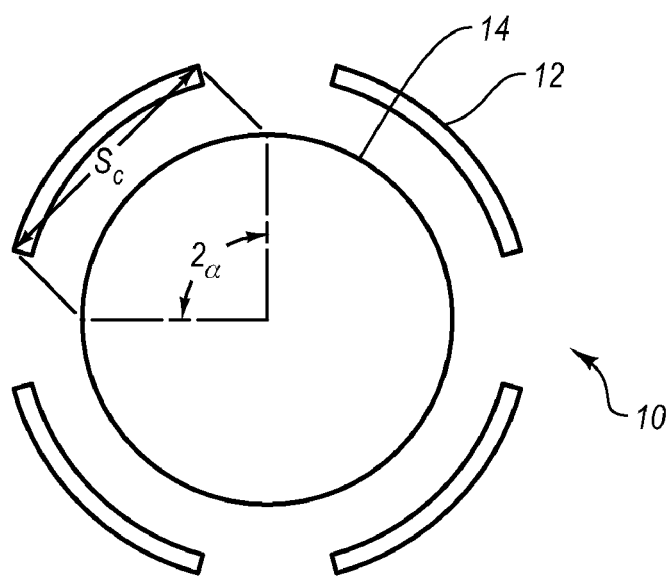

As an initial starting point, and with reference to FIGS. 4A and 4B which schematically illustrates the expansion of the tube segments from about diameter 14D to about diameter 12D, the circumference of the stent inner diameter following expansion, which should closely approximate the diameter 12D, can be calculated by:

$$U_C = \phi C * \pi \quad (1)$$

where $U_C$ is the circumference, $\phi C$ is the starting diameter, i.e., diameter 14D, and $\pi$ is approximated to 3.14. The circumference of the outer diameter of the first tube portion 12, i.e., diameter 12D, can be calculated by:

$$U_B = \phi B * \pi \quad (2)$$

where $U_B$ is the circumference, $\phi B$ is the finishing diameter, i.e., diameter 12D, and $\pi$ is approximated to 3.14. In view of this, $\phi B > \phi C$ and $U_B$ should be minimized as much as the circumference of the remainder part of the mandrel 10 is equal or smaller than the circumference $U_C$.

With continued reference to FIG. 4A, the original circumference is equal to the reduced circumference, but both radii may not be equal. As such, the equivalence of the chord length(s) are to be considered when calculating the arc length "b" of the identified tube segment 24. From FIG. 4B, generally the chord length $S_C$ can be calculated as using the following relation as follows $$S_C = 2r * \sin \alpha \quad (3)$$

$$r = \frac{\phi C}{2} \quad (4)$$

with α=45°, it is know that $$\sin 45 = \frac{\sqrt{2}}{2} \quad (5)$$

thus, the chord length of $S_C$ can be found as follows:

$$S_C = 2 * \frac{\phi C}{2} * \frac{\sqrt{2}}{2} = \frac{\phi C \sqrt{2}}{2} = \text{constant} \quad (6)$$

Figure 4C:
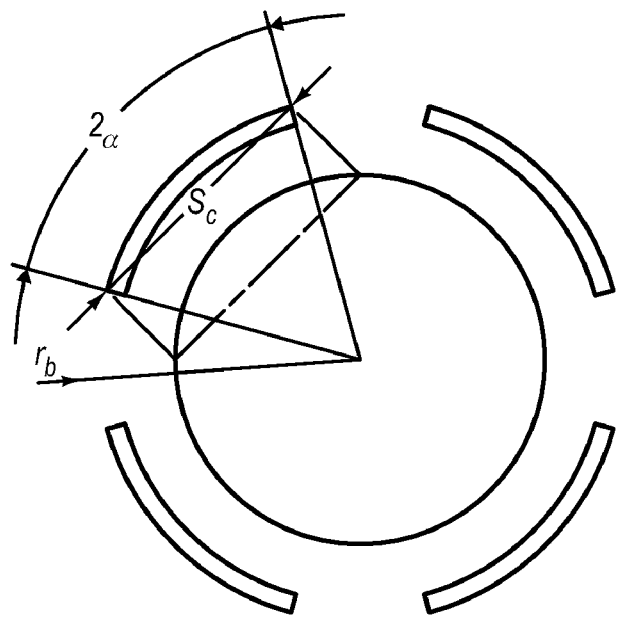
Figure 4D:
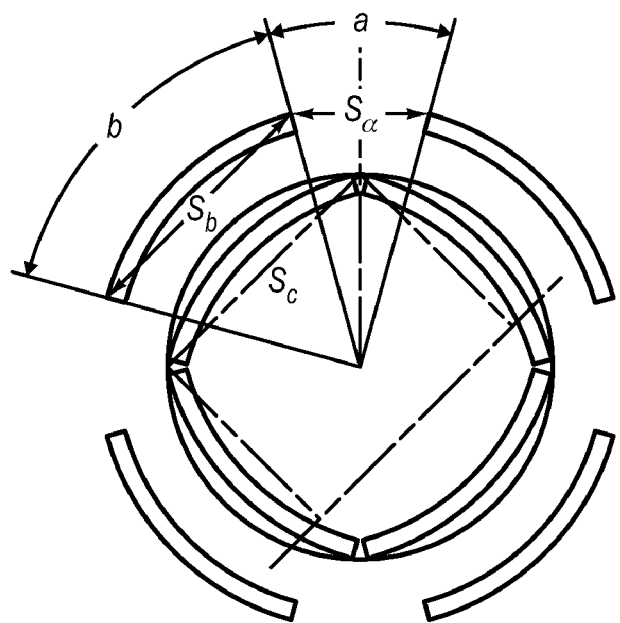

With reference to FIG. 4C, the chord length $S_C$ correlates to chord $S_b$ with a radius defined as follows:

$$r_b = \frac{\phi B}{2} \quad (7)$$

In view of the identified radius of equation 7, and out of the geometrical distribution identified in FIGS. 4A-4C, the following can be deduced:

$$S_C = S_b = 2r_b * \sin\alpha \quad (8)$$

thus $$2 * \frac{\phi B}{2} * \sin\alpha = S_C = \text{constant} \quad (9)$$

and $$\sin\alpha = \frac{S_C}{\phi B} \quad (10)$$

and so $$\alpha = \arcsin\left(\frac{S_C}{\phi B}\right) \quad (11)$$

With the calculation of arc α of chord lengths $S_c$ and $S_b$ it is possible to calculate the width of size "a" of the slot or gap 26 using the schematic illustration of FIG. 4C with the following. The circumference $U_c$ of the reduced tube, i.e., diameter 14D, should be equal to or bigger than the four tube segments 24 added together. This means, therefore, $$U_C \geq 4*b \quad (12)$$

$U_B$ and $S_b$ are known and defined by, respectively, $$U_B = 4b + 4a \quad (13)$$

$$b = \frac{r_b * \pi * \alpha}{90} \quad (14)$$

Thus, solving for a, we obtain $$a = \frac{U_B - 4b}{4} \quad (15)$$

With the arc lengths calculated, i.e., values for a and b, the mandrel member 40 illustrated in FIG. 3 can be manufactured, with the gap or slots 26 formed to obtain the desired stent expansion.

The present invention may be embodied in other specific forms without departing from its spirit or essential characteristics. For example, slight modifications of the mandrel are contemplated and possible and still be within the spirit of the present invention and the scope of the claims. The scope of the invention is, therefore, indicated by the appended claims rather than by the foregoing description.

What is claimed is:

1. A mandrel usable for expanding a medical device, the mandrel comprising:
    an elongate first tube portion having a first lumen and a first tube diameter;
    an elongate second tube portion extending from the first tube portion, the second tube portion being configured to receive a medical device and having a second tube diameter smaller than the first tube diameter, the second tube portion having a plurality of tube segments separated by a plurality of slots and a second lumen in communication with the first lumen, at least a portion of the plurality of tube segments being moveable outwardly to expand the medical device placed upon the second tube portion; and
    a transition region disposed between the first tube portion and the second tube portion, the plurality of tube segments and the plurality of slots extending from the transition region toward a cone at a distal end of the second tube portion, the cone being configured to limit outward movement of the plurality of tube segments, a proximal end of the tube segments and a proximal end of the plurality of slots terminating at the transition region and a distal end of the tube segments and a distal end of the plurality of slots terminating at the cone.

2. The mandrel of claim 1, wherein the second tube portion receives the medical device upon an outer surface of the second tube portion.

3. The mandrel of claim 1, wherein at least one of the plurality of slots includes a strain reduction feature.

4. The mandrel as recited in claim 1, wherein each slot has a width upon expansion defined by the equation $$a = \frac{U_B - 4b}{4}$$

where a is the width of each slot, $U_B$ is the outer diameter of the first tube portion and b is the arc length of a tube segment of the plurality of tube segments.

5. The mandrel as recited in claim 4, wherein an internal diameter of the medical device placed upon the second tube portion substantially equals $U_B$.

6. The mandrel as recited in claim 4, wherein a radii of each tube segment of the plurality of tube segments of the second tube portion is different to a radii of the first tube portion.

7. A system for manufacturing a medical device comprising:
    a mandrel comprising:
        a first tube portion having a first lumen and a first tube diameter; and
        a second tube portion configured to receive a medical device, the second tube portion having a second tube diameter smaller than the first tube diameter, a plurality of tube segments separated by a plurality of slots, and a second lumen in communication with the first lumen, the tube segments and the plurality of slots terminating at a transition region disposed between the first tube portion and the second tube portion, a proximal end of the tube segments and a proximal end of the plurality of slots terminating at the transition region and a distal end of the tube segments and a distal end of the plurality of slots terminating at a cone disposed at a distal end of the second tube portion, the cone being configured to limit outward movement of the plurality of tube segments; and an expansion member slidably receivable within at least a portion of the first lumen and the second lumen, the expansion member advanceable within the second lumen to move the plurality of tube segments radially outwardly to expand the medical device.

8. The system of claim 7, wherein the plurality of slots are arranged longitudinally along the second tube portion.

9. The system of claim 7, wherein the second tube portion has a circumference and the plurality of slots are spaced at ninety degree intervals around the circumference of the second tube portion.

10. The system of claim 7, wherein the expansion member is another mandrel.

11. A system for manufacturing a stent comprising:
a first mandrel comprising:
  a first tube portion having a first lumen and a first tube diameter; and
  a second tube portion configured to receive a stent, the second tube portion having a second tube diameter smaller than the first tube diameter, a plurality of tube segments separated by a plurality of slots, and a second lumen in communication with the first lumen, the tube segments and the plurality of slots terminating at a transition region disposed between the first tube portion and the second tube portion, a proximal end of the tube segments and a proximal end of the plurality of slots terminating at the transition region and a distal end of the tube segments and a distal end of the plurality of slots terminating at a cone disposed at a distal end of the second tube portion, the cone being configured to limit outward movement of the plurality of tube segments; and
a second mandrel slidably receivable within at least a portion of the first lumen and the second lumen, the second mandrel being advanceable within the second lumen to move the plurality of tube segments radially outwardly to expand the stent.

12. The system of claim 11, wherein one end of each of the plurality of slots has a generally circular strain reducing feature.

13. The system of claim 11, wherein the plurality of slots are equidistantly spaced around the second tube portion.

14. The system of claim 11, further comprising a stent received on the second tube portion of the first mandrel, wherein the stent is a self expanding stent.

15. The system of claim 11, wherein the second mandrel comprises:

a third tube portion having a third lumen and a third tube diameter; and
a fourth tube portion having a fourth tube diameter smaller than the third tube diameter, a second plurality of tube segments separated by a second plurality of slots, and a fourth lumen in communication with the third lumen.

16. The system of claim 15, wherein the fourth tube portion of the second mandrel is slidably received within the first lumen and a portion of the second lumen of the first mandrel.

17. A method of expanding the diameter of a medical device, the method comprising:
positioning a first mandrel having a first tube portion and a second tube portion for receiving a medical device, a first tube portion diameter of the first tube portion being larger than a second tube portion diameter of the second tube portion, a transition region being disposed between the first tube portion and the second tube portion, a plurality of tube segments and a plurality of slots extending from the transition region toward a cone at a distal end of the second tube portion, the cone being configured to limit outward movement of the plurality of tube segments, a proximal end of the tube segments and a proximal end of the plurality of slots terminating at the transition region and a distal end of the tube segments and a distal end of the plurality of slots terminating at the cone;
placing the medical device over a portion of the second tube portion; and
inserting an expansion member within at least a portion of the first tube portion and the second tube portion, the expansion member increasing the second tube portion diameter to increase the diameter of the medical device as the plurality of tube segments move outwardly.

18. The method of claim 17, wherein inserting the expansion member comprises inserting a second mandrel.

19. The method of claim 17, further comprising annealing the medical device upon the first mandrel after the medical device has been expanded by the first mandrel.

20. The method of claim 19, further comprising:
removing the expansion member from within at least a portion of the first tube portion and the second tube portion following annealing of the medical device; and
expanding the medical device upon a second mandrel to increase the outer diameter of the medical device.

21. The method of claim 20, wherein the second mandrel has a third tube portion and a fourth tube portion, at least one of the third tube portion and the fourth tube portion having a diameter equal to or larger than the diameter of the first tube portion and the second tube portion, and wherein expanding the medical device comprises:
placing the annealed medical device on the second mandrel; and
inserting another expansion member within at least a portion of the third tube portion and the fourth tube portion, the another expansion member increasing the fourth tube portion diameter to increase the diameter of the medical device.

* * * * *